US012788440B2

(12) United States Patent
Buse

(10) Patent No.: US 12,788,440 B2
(45) Date of Patent: Nov. 10, 2026

(54) SACROILIAC SCREW

(71) Applicant: CoreLink, LLC, St. Louis, MO (US)

(72) Inventor: John Buse, Washington, MO (US)

(73) Assignee: CORELINK, LLC, St. Louis, MO (US)

( * ) Notice: Subject to any disclaimer, the term of this patent is extended or adjusted under 35 U.S.C. 154(b) by 164 days.

(21) Appl. No.: 18/653,697

(22) Filed: May 2, 2024

(65) Prior Publication Data

US 2025/0099135 A1 Mar. 27, 2025

Related U.S. Application Data

(60) Provisional application No. 63/499,591, filed on May 2, 2023.

(51) Int. Cl.
*A61B 17/70* (2006.01)
*A61B 17/86* (2006.01)

(52) U.S. Cl.
CPC ...... *A61B 17/7007* (2013.01); *A61B 17/7055* (2013.01); *A61B 17/8605* (2013.01); *A61B 17/8635* (2013.01); *A61B 17/866* (2013.01)

(58) Field of Classification Search
CPC ............ A61B 17/7007; A61B 17/7055; A61B 17/866
See application file for complete search history.

(56) References Cited

U.S. PATENT DOCUMENTS

| | | | | |
|---|---|---|---|---|
| 5,334,205 | A * | 8/1994 | Cain | A61B 17/1742 606/86 R |
| 6,005,161 | A * | 12/1999 | Brekke | A61L 27/3641 424/422 |
| 10,595,917 | B2 * | 3/2020 | Loftus | A61B 17/888 |
| 11,166,821 | B2 * | 11/2021 | Sazy | A61F 2/30988 |
| 2006/0036322 | A1 | 2/2006 | Reiley | |
| 2007/0270879 | A1 * | 11/2007 | Isaza | A61B 17/1739 606/104 |
| 2011/0087296 | A1 | 4/2011 | Reiley et al. | |
| 2014/0012334 | A1 | 1/2014 | Armstrong et al. | |
| 2019/0343565 | A1 | 11/2019 | Tempco et al. | |
| 2021/0153911 | A1 | 5/2021 | Stuart et al. | |
| 2022/0273446 | A1 | 9/2022 | Stuart et al. | |
| 2022/0354665 | A1 | 11/2022 | Mesiwala et al. | |
| 2023/0263554 | A1 | 8/2023 | Stuart et al. | |
| 2023/0270559 | A1 | 8/2023 | Mesiwala et al. | |
| 2024/0407810 | A1 | 12/2024 | Mesiwala et al. | |
| 2025/0177011 | A1 | 6/2025 | Stuart et al. | |

* cited by examiner

*Primary Examiner* — Christian A Sevilla
(74) *Attorney, Agent, or Firm* — Stinson LLP

(57) ABSTRACT

A sacroiliac screw includes a tip, a head, a shank, and at least one screw thread that are integrally formed as a one-piece, monolithic component by additive manufacturing. The sacroiliac screw is configured to be implanted into the ilium bone and through the sacroiliac joint. The head has a frustoconical shape having an outer annular surface tapering from a proximal end to a distal end of the head. A washer may be received on the head of the screw.

20 Claims, 12 Drawing Sheets

SACROILIAC SCREW

CROSS-REFERENCE TO RELATED APPLICATION

The application claims priority to U.S. Provisional Ser. No. 63/499,591 filed May 2, 2023.

FIELD OF THE DISCLOSURE

The present disclosure generally relates to a sacroiliac screw.

BACKGROUND OF THE DISCLOSURE

A sacroiliac screw is a medical device used for the stabilization of the sacroiliac joint. The screw is designed to be implanted into the ilium bone and through the sacroiliac joint to provide stability and support to the joint.

SUMMARY OF THE DISCLOSURE

Features of a sacroiliac screw are described and shown herein.

DETAILED DESCRIPTION OF THE DISCLOSURE

Figure 1:
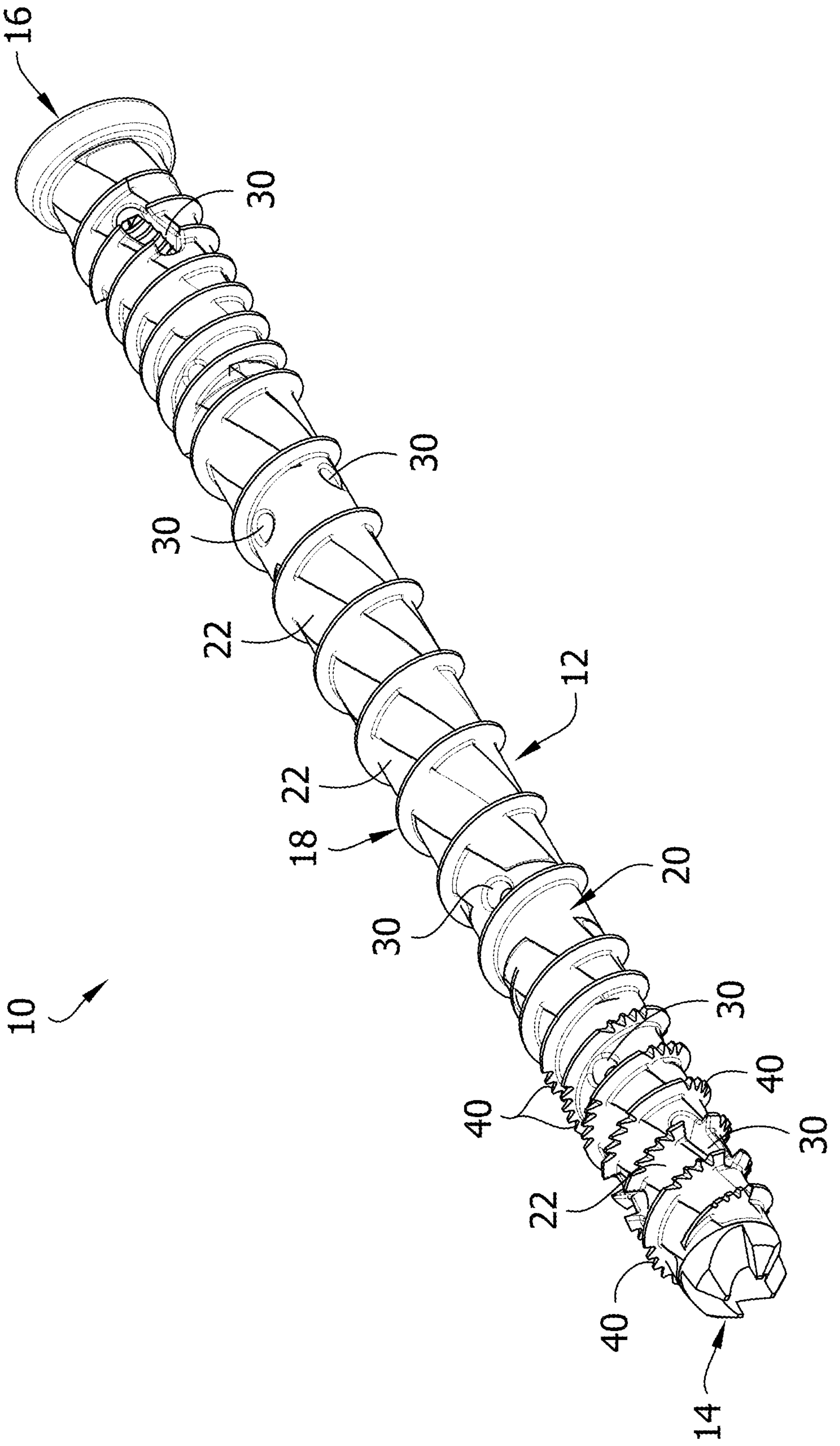
FIG. 1 is a perspective of one embodiment of a sacroiliac screw.
Figure 2:
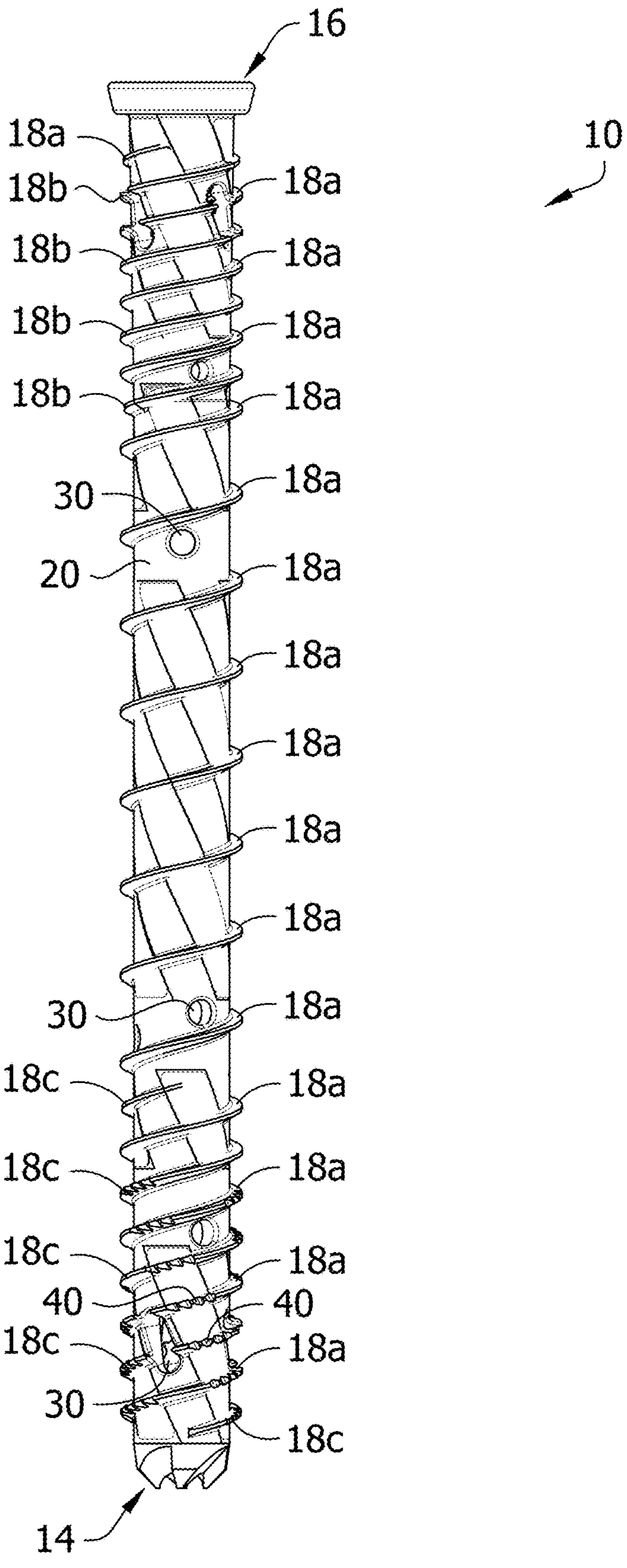
FIG. 2 is a top plan of the screw in FIG. 1.
Figure 3:
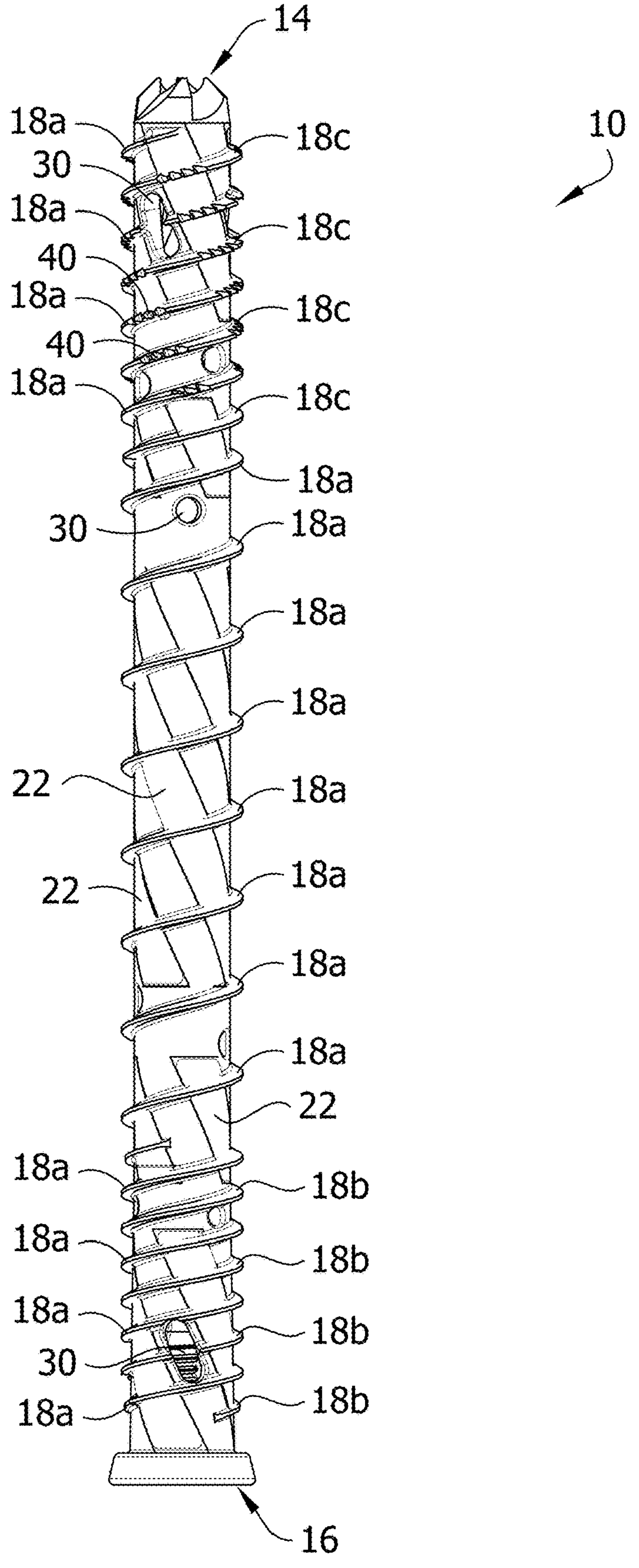
FIG. 3 is a bottom plan of the screw in FIG. 1.
Figure 4:
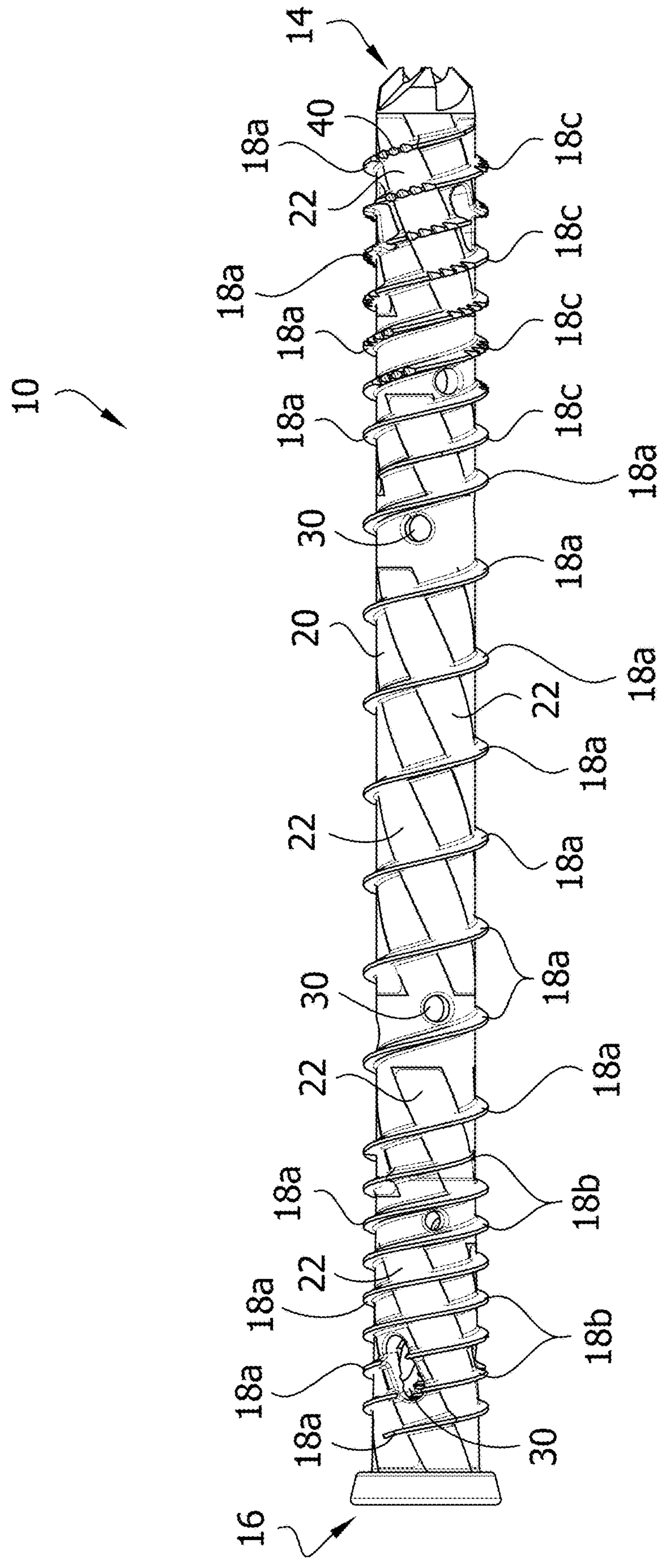
FIG. 4 is a left elevational view of the screw in FIG. 1.
Figure 5:
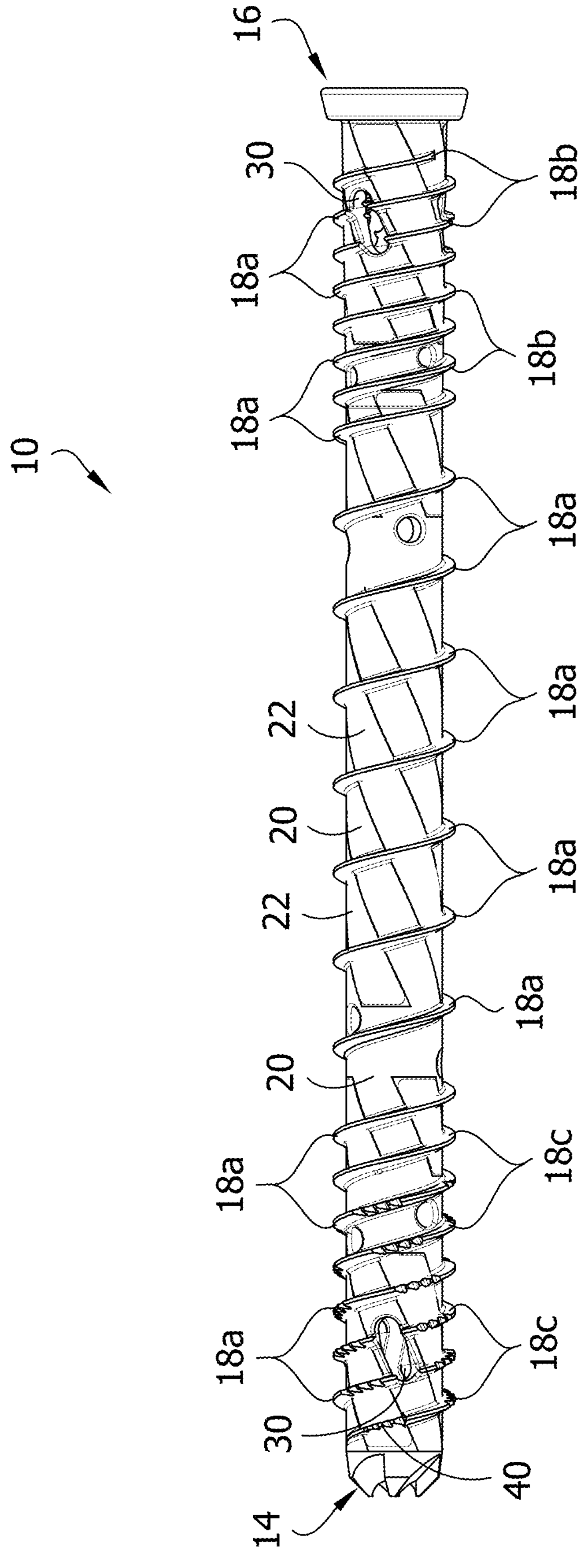
FIG. 5 is a right elevational view of the screw in FIG. 1

Referring to FIG. 1, an illustrated embodiment of a sacroiliac (SI) screw designed and constructed according to one or more teachings of the present disclosure is generally indicated at reference numeral 10. The screw 10 includes a shank 12, a tip 14, a head 16, and one or more screw threads 18, each indicated generally. Each of these components are integrally formed so that the screw 10 is formed as a one-piece, monolithically formed component. The screw 10 may be formed by additive manufacturing, such as by direct metal laser sintering or by electron beam melting processes as is generally known. The illustrated screw is designed and constructed for the stabilization and/or fusion of the sacroiliac joint.

Figure 6:
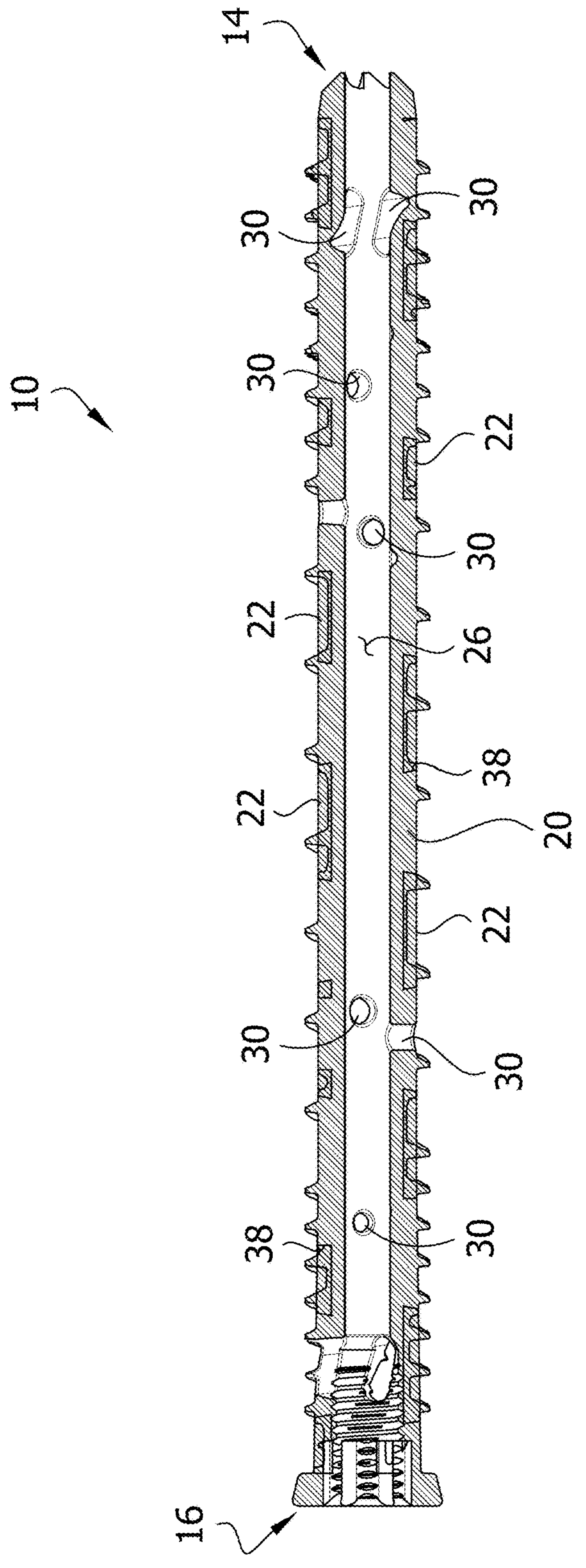
FIG. 6 is a longitudinal section taken through the screw.

The shank 12 includes a shank body 20 and exposed open-cell metal foam 22 integrally formed on the shank body. The shank body 20 extends from the tip 14 (or adjacent thereto) to the head 16 (or adjacent thereto). The shank body 20 has a generally rod shape having an outer diameter and a length. As a non-limiting example, the outer diameter of the shank body 20 may be from about 9 mm to about 15 mm, such as 9.5 mm or 11.5 mm or 14.5 mm. As a non-limiting example, the length of the shank body may be from about 30 mm to about 110 mm in 5 mm increments. The dimensions of the shank body 20 may be dependent on the patient and the specific surgical procedure. An outer surface of the shank body 20 may be relatively smooth compared to an outer surface of the open-cell metal foam 22. As shown in FIG. 6, the screw 10 may be cannulated, whereby the shank body 20 defines a longitudinal internal passage 26 for receiving a guidewire or k-wire or other device, as is generally known in the art. The shank body 20 provides desired structural support, including desired bending strength, for the screw.

The shank body 20 further defines openings 30 (e.g., fenestrations) extending through the outer surface to the internal passage 26 to enable bone growth therein. The openings 30 may be of suitable shapes and sizes. In the illustrated embodiment, the openings 30 are outside the boundaries of discrete areas of the open-cell metal foam 22. In the illustrated embodiment, openings 30 at adjacent the tip 14 and the head 16 are generally slot-shaped having lengths extending at offset angles relative to the longitudinal axis of the shank 12, such that the slot-shaped openings extending longitudinally and circumferentially. The number, size and shape of the openings 30 are such that there is at least one open area at every angle around the 360-degree circumference of the shank body 20. In other words, around the circumference of the screw body 20, there is at least one opening 30 at some longitudinal position enabling bone growth. In this way, the screw 10 enables bone growth around the entire 360-degrees circumference of the screw body 20 to facilitate and enhance screw retention in bone.

Figure 7:
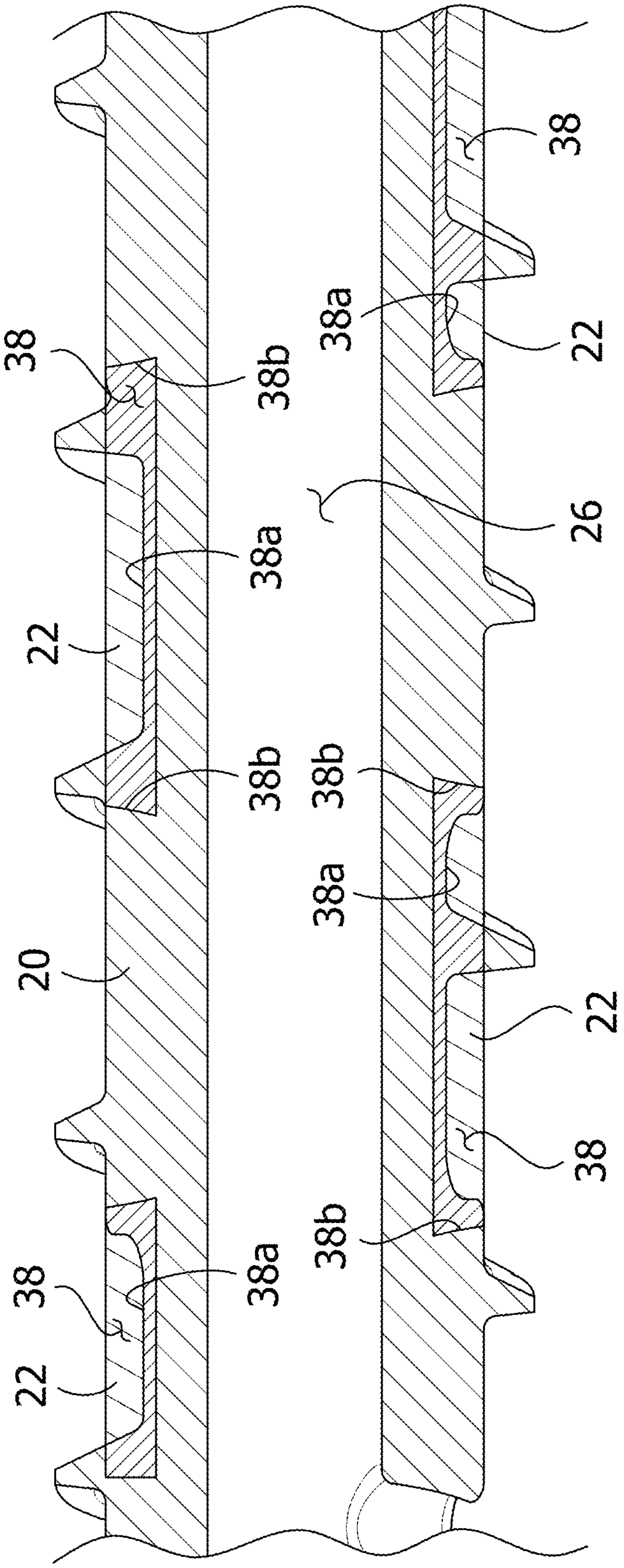
FIG. 7 is an enlarged, partial view of FIG. 6.

In the illustrated embodiment, the open-cell metal foam 22 comprises a plurality of open-cell foam portions at discrete areas on the shank 12 so that the outer surface of the shank 12 includes discrete areas of open-cell metal foam 22 and discrete areas of the shank body 20. As used herein, "open-cell metal foam" is a porous structural component having a relatively roughened surface, an apparent randomized filament arrangement, and cell sizes and shapes forming an interconnected network or labyrinth to facilitate bone in-growth. From a sectional view, such as shown in FIGS. 6 and 7, the open-cell metal foam 22 appears to be disposed in pockets or recesses 38 defined by the shank body 20. As explained above, the screw 10 may be formed from additive manufacturing, such that the features of the screw are integrally formed. The open-cell metal foam 22 is not received in the pockets or recesses because the pockets or recesses are formed as the open-cell metal foam is formed according to additive manufacturing processes. Accordingly, the description of the open-cell metal foam 22 being disposed in pockets or recesses 38 defined by the shank body 20 should be understood in a broad sense. In the illustrated embodiment, the recesses or pockets 38 of the shank body 20 have a radially inward surface 38*a* and side walls 38*b* extending radially from the bottom surface such that the open-cell metal foam 22 is not in communication with the internal passage.

In the illustrated embodiment, the open-cell metal foam portions 22 are elongate having longitudinal axes that are angularly offset from the longitudinal axis of the shank 12, so that the portions extend at least partially circumferentially in addition to longitudinally. The number, size and shape of the open-cell metal foam portions 22 are such that there is open-cell metal foam 22 at every angle around the 360-degree circumference of the shank body 20. In other words, around the circumference of the shank body 20, there is at least one open-cell metal foam portion 22 at one or more longitudinal position enabling bone ingrowth into the open-cell metal foam. In this way, the screw 10 enables bone growth around the entire 360-degrees circumference of the screw body 20 to facilitate and enhance screw retention in bone.

In the illustrated embodiment, the screw thread 18 comprises more than one screw thread. In particular, the screw thread 18 includes a lengthwise thread 18*a*, a proximal screw thread 18*b*, and a distal screw thread 18*c*. The lengthwise thread extends from adjacent the tip 14 (i.e., adjacent the distal end of the shank body 20) to adjacent the head 16 (i.e., adjacent the proximal end of the shaft bod). Thus, the lengthwise thread 18*a* extends more than a majority, and in one embodiment more than 85%, of the length of the shank body 20. The lengthwise thread 18*a* may have a uniform pitch along its length or the thread may have a variable pitch. In the illustrated embodiment, the lengthwise thread has a variable pitch, as explained in more detail below.

The distal thread 18*c* extends from adjacent the tip 14 to a longitudinal location that is distal of the mid-length of the shank body 20. Accordingly, the distal thread is contained within a distal portion of the shank body 20. The distal thread 18*c* may have a uniform pitch along its length or the distal thread may have a variable pitch. In the illustrated embodiment, the distal thread 18*c* has a uniform pitch. The distal thread 18*c* is intertwined with the lengthwise thread 18*a* at a distal portion of the shank body 20. In particular, a turn of the distal thread 18*c* is disposed between adjacent turns of the lengthwise thread 18*a*. In the illustrated embodiment, the pitch of the distal thread 18*c* is equal to the pitch of the lengthwise thread 18*a* at the distal portion of the shank body 20, and the turns of the distal thread 18*c* are spaced mid-way between corresponding adjacent turns of the lengthwise body 18*a*. Together, the distal thread 18*c* and the lengthwise thread 18*a* at the distal portion of the shank body 20 constitute a distal screw thread portion of the screw thread 18.

In the illustrated embodiment, the distal screw thread portion defines serrations 40 to enable digging or cutting of the distal screw thread portion into bone. The serrations 40 are disposed in groupings around turns of the distal screw thread portion at suitable locations to define stripes of serrations extending longitudinally and circumferentially. In the illustrated example, the groupings of serrations 40 are disposed over and on or within the boundaries of the open-cell metal foam 22.

The proximal thread 18*b* extends from adjacent the head 14 to a longitudinal location that is proximal of the mid-length of the shank body 20. Accordingly, the proximal thread is contained within a proximal portion of the shank body 20. The proximal thread 18*b* may have a uniform pitch along its length or the thread may have a variable pitch. In the illustrated embodiment, the proximal thread 18*b* has a uniform pitch. The proximal thread 18*b* is intertwined with the lengthwise thread 18*a* at a proximal portion of the shank body 20. In particular, a turn of the proximal thread 18*b* is disposed between adjacent turns of the lengthwise thread 18*a*. In the illustrated embodiment, the pitch of the proximal thread 18*b* is equal to the pitch of the lengthwise thread 18*a* at the proximal portion of the shank body 20, and the turns of the proximal thread are spaced mid-way between corresponding adjacent turns of the lengthwise body. Together, the proximal thread 18*b* and the lengthwise thread 18*a* at the proximal portion of the shank body 20 constitute a proximal screw thread portion of the screw thread 18.

In the illustrated embodiment, a central screw thread portion of the screw thread 18 is disposed between the distal and proximal screw thread portions. The central thread portion consists of the lengthwise thread 18*a* only because the distal thread terminates 18*c* adjacent a distal end of the central thread portion, and the proximal thread 18*b* terminates adjacent a proximal end of the central thread portion.

The pitch of the distal screw thread portion is greater than the pitch of the proximal screw thread portion. The pitch of the central screw thread portion is greater than both the distal and proximal screw thread portions. Through this construction, the screw thread imparts and compressive load when screwed into the ilium and sacrum.

The screw thread 18 is integrally formed and directly connected to the shank body 20. Referring to FIG. 7, segments of the screw thread 18 are connected directly to the outer surface of the shank body 20 or the radially inner surface 38*a* of the shank body that partially defines the pockets 38. Thus, the radially inner end of the screw thread is connected directly the shank body 20 (e.g., radially inner surface 38*a*), and the open-cell metal foam 22 is not disposed radially between the radially inner end of the screw thread and the radially inner surface of the shank body. This construction provides structural support to the thread 18, including shear strength to inhibit shearing off of the thread from the shank. In the pockets 38, the open-cell metal foam 22 is directly connected to and integrally formed the proximal and distal surfaces of the screw thread 18 and the radially inner surfaces 38*a* of the shank body 20.

In the illustrated embodiment, the tip 14 of the screw 10 is fluted or otherwise formed to enable cutting into bone. Also in the illustrated embodiment, the head 16 of the screw 10 defines a shoulder suitable for receiving a washer thereon. The head 16 has a frustoconical shape having an outer (or lateral) annular surface tapering from a proximal end to a distal end of the head. A distal end of the head 16 is has a generally planar surface extending radially outward from the shank body 20. A proximal end of the head 16 has a generally planar surfaces and defines an opening leading to an internal passage through the head. The diameter of the head 16 at its proximal end of greater than the diameter of the head at its distal end. The entirety of the outer (or lateral) annular surface of the of the head 16 is disposed radially outward of the shank body 20, and in one embodiment, radially outward of the thread(s) 18*a*, 18*b*, 18*c*. The head 16 has rounded or radiused proximal and distal edges where the proximal end meets the outer (or lateral annular surface and the distal end meets the outer (or lateral) annular surface, respectively.

Figure 8:
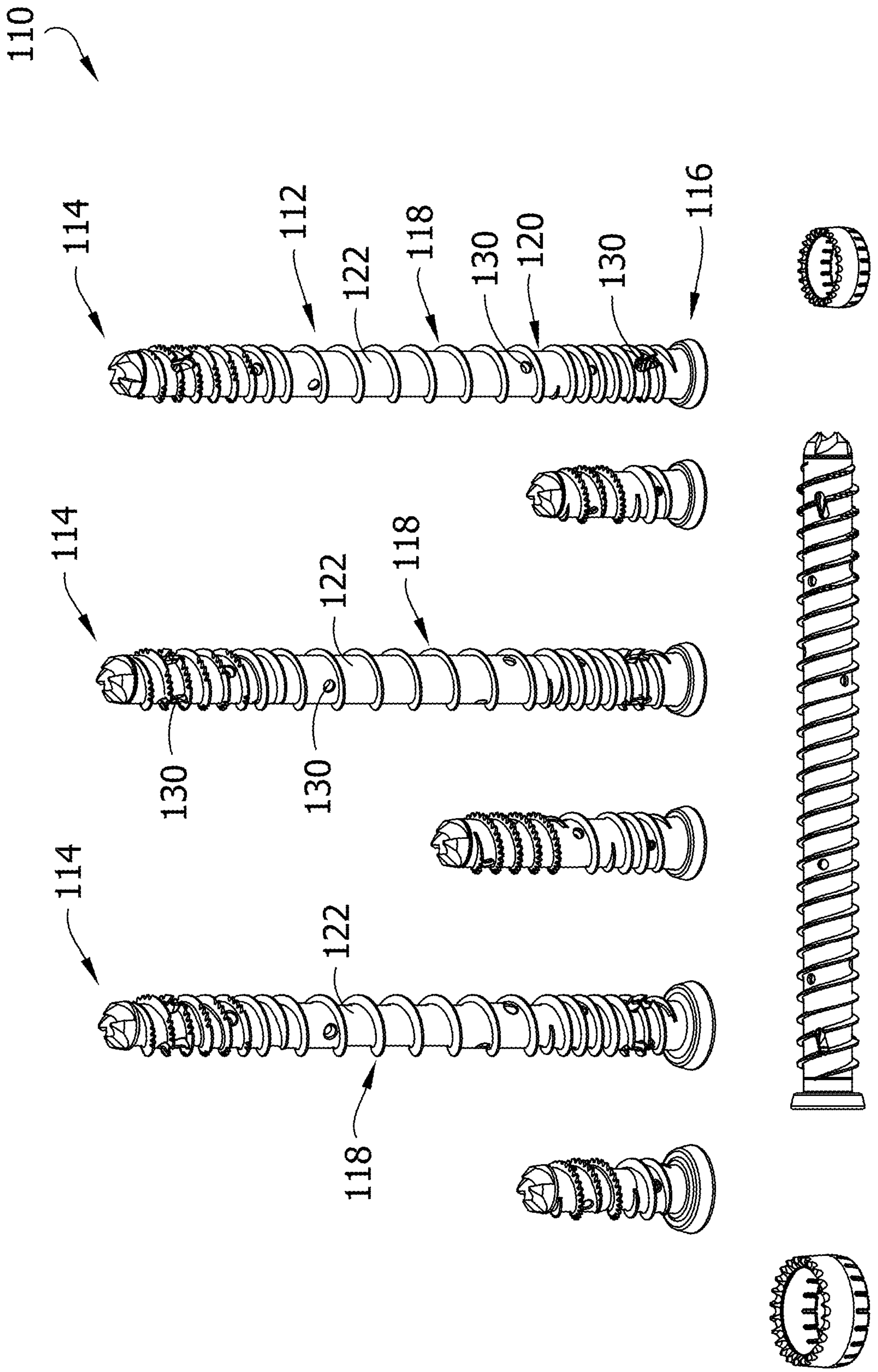
FIG. 8 illustrates several examples of another embodiment of the sacroiliac screw.

Referring to FIG. 8, other embodiments of SI screws are generally indicated at reference numeral 110. The SI screws 110 may be identical to the screw 10 described above, except as described below. Thus, the teachings set forth above, unless explicitly different than the description below, apply equally to the screws 110.

The primary different between the screws 110 and screw 10 is that open-cell metal foam 122 is disposed on substantially the entirety (e.g., at least 85%, such as at least 85% or at least 90% or at least 95% or at least 98% or at least 99% or about 100%) of the outer surface area of the shank body 120 that is not occupied by the screw thread 118 or openings 130. Thus, unlike the open-cell metal foam 22 of the screw 10, the open cell metal foam 122 of this embodiment is not disposed in stripes or discrete areas of the shank body 120, but covers substantially the entirety of the shank body 120.

Also shown in FIG. 8, are washers 150 configured to be received on the heads of the screws 110. These washers 150 are described in more detail below with respect to FIGS. 9 and 10.

Figure 9:
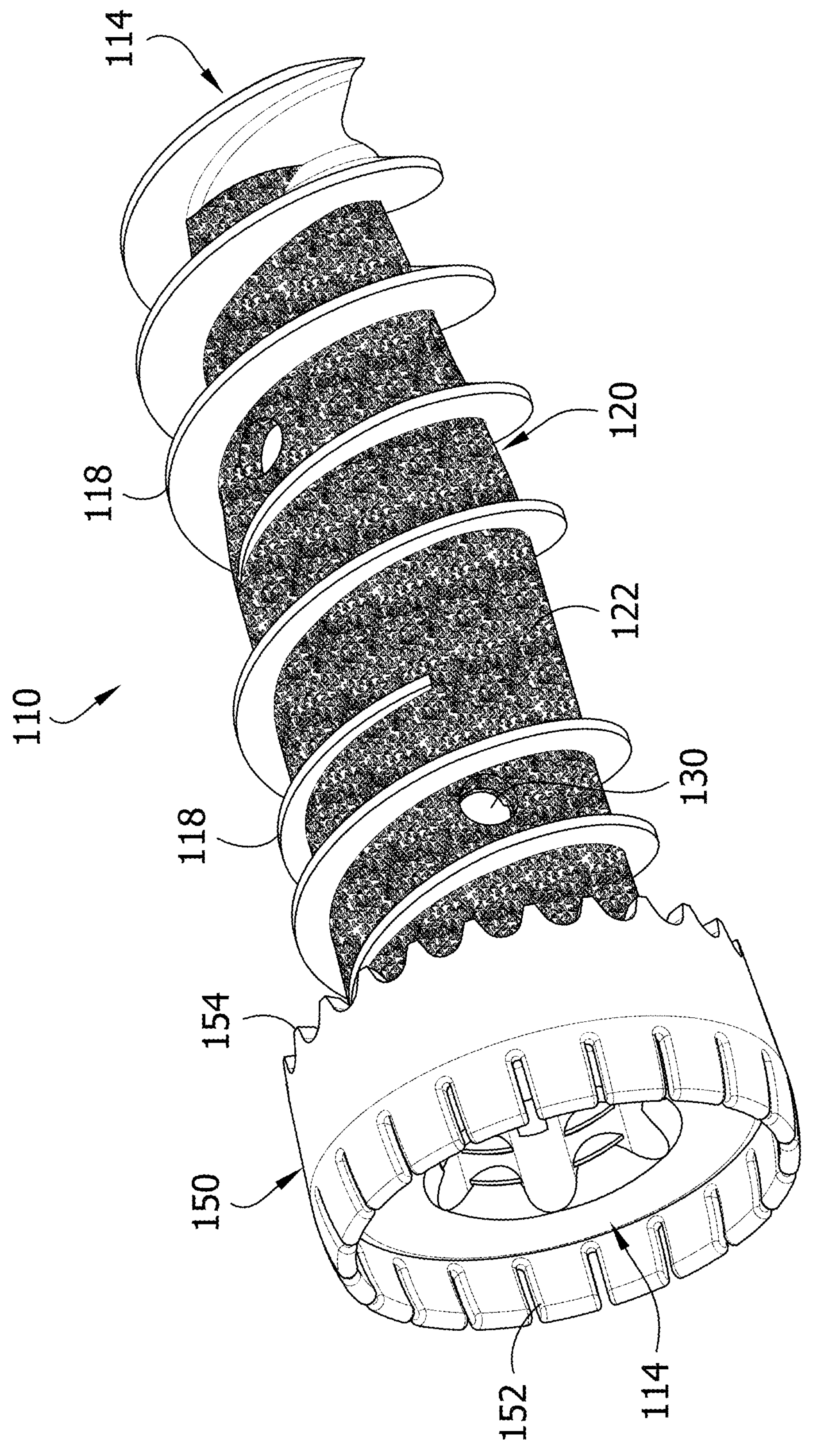
FIG. 9 is a perspective of one embodiment of the sacroiliac screw including a washer received thereon.
Figure 10:
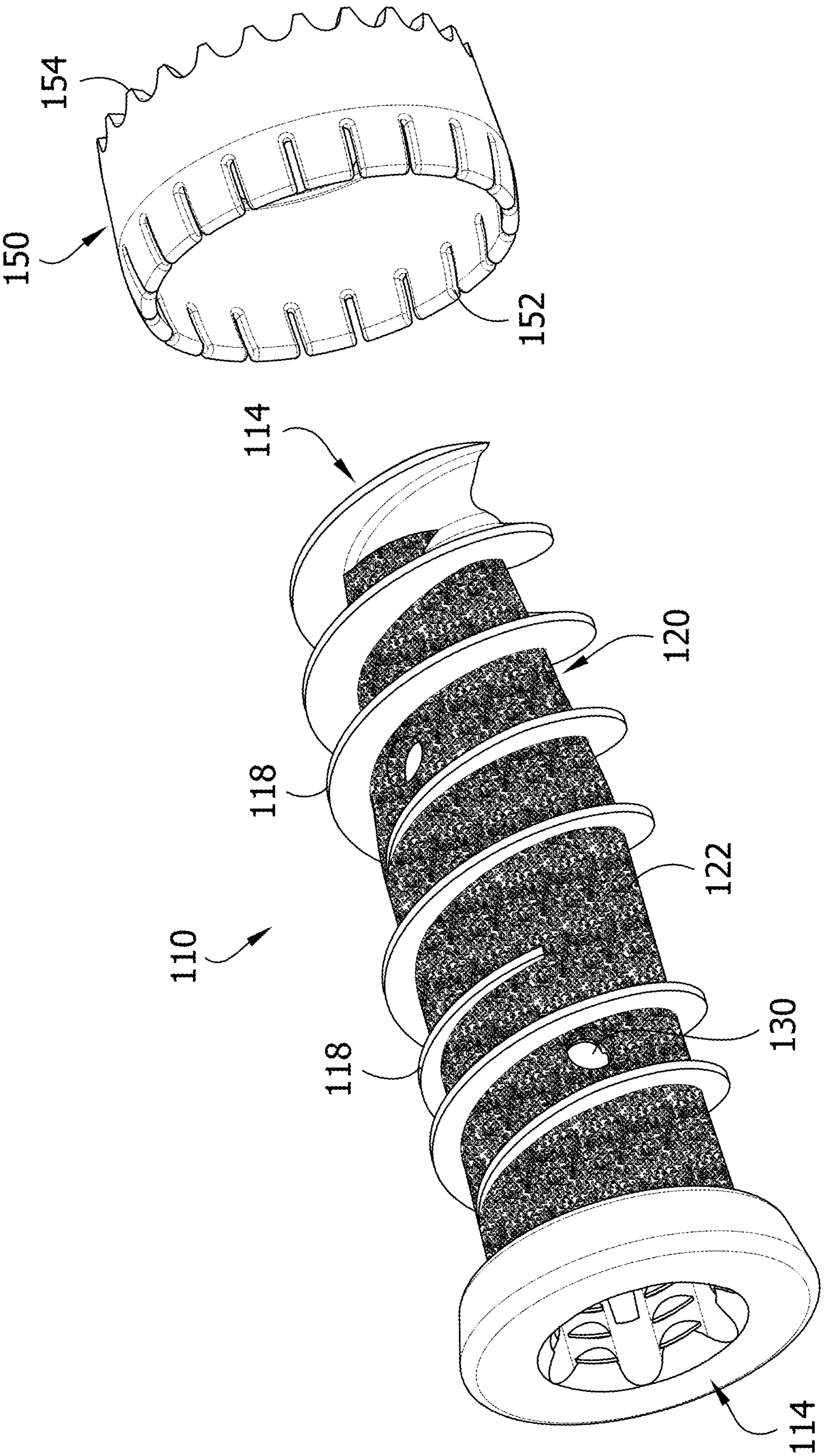
FIG. 10 is an exploded view of FIG. 9.

Referring to FIG. 9, one of the screws 100 of FIG. 8 is shown in detail, including the washer 150 received on the head 116. As shown in FIG. 10, similar to the first embodiment, the head 116 screw 110 defines a shoulder suitable for receiving a washer thereon. The head 116 has a frustoconical shape having an outer (or lateral) annular surface tapering from a proximal end to a distal end of the head. A distal end of the head 116 is has a generally planar surface extending radially outward from the shank body 120. A proximal end of the head 116 has a generally planar surfaces and defines an opening leading to an internal passage through the head. This internal passage is configured to receive a tool for inserting the screw 110 in bone of a patient. The diameter of the head 116 at its proximal end of greater than the diameter of the head at its distal end. The entirety of the outer (or lateral) annular surface of the of the head 116 extends radially outward of the shank body 120, and in one embodiment, radially outward of the thread(s) 118. The head 116 has rounded (or radiused) proximal and distal edges where the proximal end meets the outer (or lateral annular surface and the distal end meets the outer (or lateral) annular surface, respectively.

Figure 11:
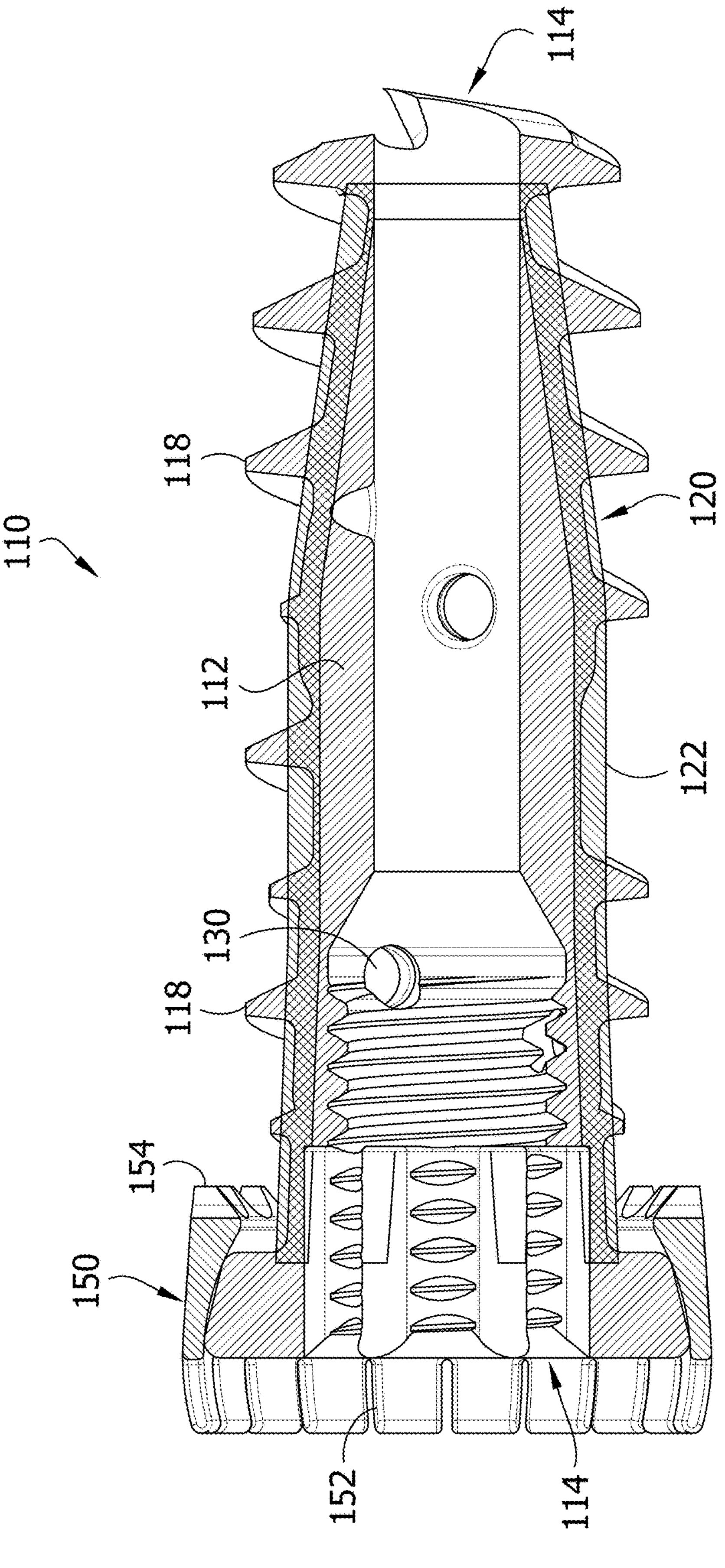
FIG. 11 is a cross section of FIG. 9.
Figure 12:
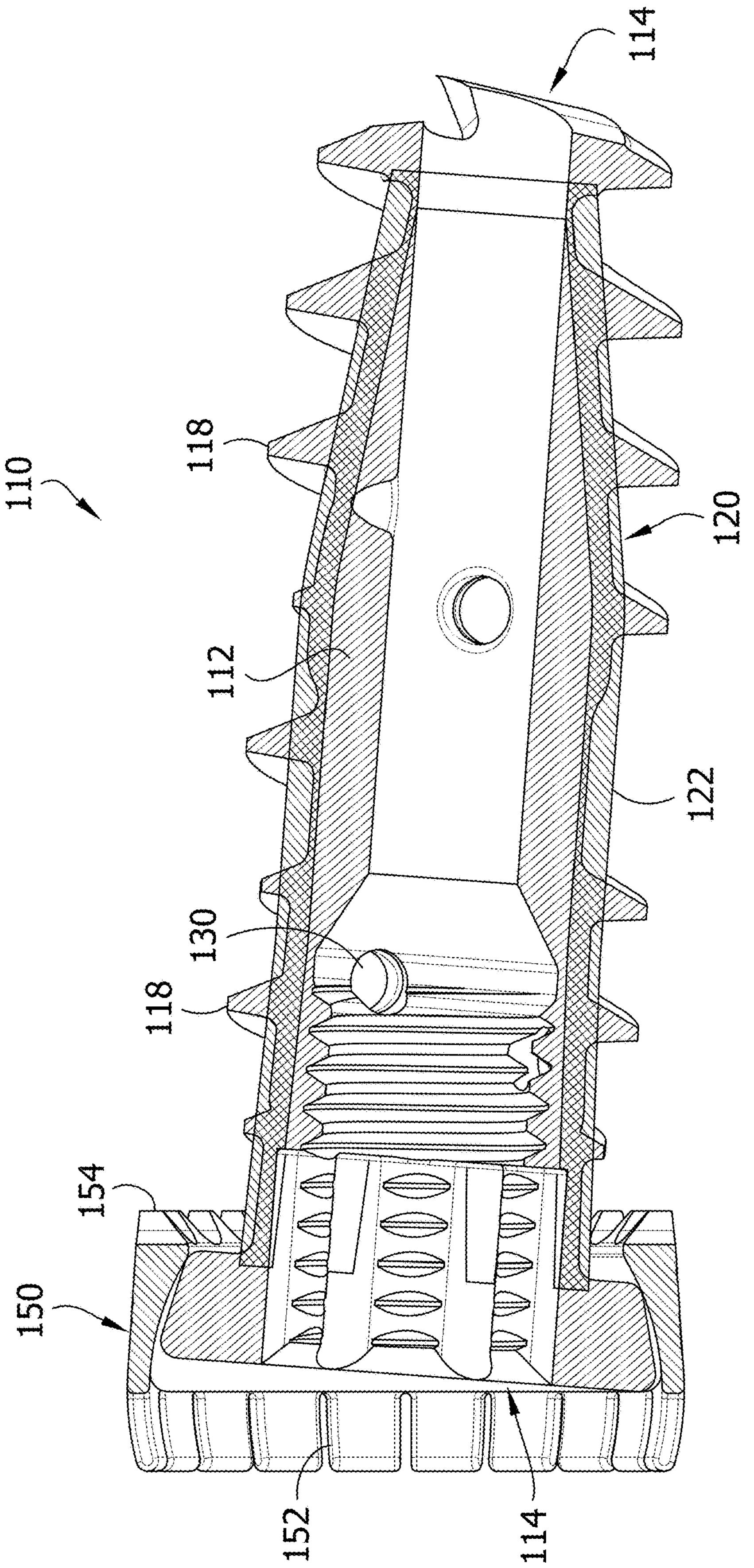
FIG. 12 is similar to FIG. 11, but with the screw angulated relative to the washer.

As shown in FIGS. 9 and 10, the washer 150 has an annular shaped body with a proximal end margin defining a plurality of axially-extending slots 152 spaced apart circumferentially, and a distal end margin defining a plurality of teeth 154 spaced apart circumferentially. The slots 152 enable the proximal end margin to radially expand to enable the washer 150 to snap onto the head 116 as the washer slides proximally along the screw shank and over the head. The teeth 154 enable the distal end margin to dig into bone as the screw is into the bone. As shown in FIG. 11, the interior of the washer 150 is rounded (i.e., concave) in cross section, and the proximal and distal edges of the head 116 engage the concave interior of the washer to enable the washer to pivot on the head. Moreover, as can be seen, the outer annular surface of the head 116 between the proximal and distal edges does not engage the interior of the washer 150.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A sacroiliac screw comprising:
a tip;
a head;
a shank extending distally from the head to the tip, the shank including a shank body and open-cell metal foam at least partially covering the shank body; and
at least one screw thread circumscribing the shank,
wherein the tip, the head, the shank, and the at least one screw thread are integrally formed as a one-piece, monolithic component by additive manufacturing,
wherein the sacroiliac screw is configured to be implanted into the ilium bone and through the sacroiliac joint,
wherein the head has a frustoconical shape having an outer annular surface tapering from a proximal end to a distal end of the head.

2. The sacroiliac screw set forth in claim 1, wherein the head has a distal end having a generally planar surface extending radially outward from the shank body.

3. The sacroiliac screw set forth in claim 2, wherein the head has a proximal end having generally planar surface, wherein the proximal end of the head has a diameter greater than a diameter of the distal end of the head.

4. The sacroiliac screw set forth in claim 3, wherein an entirety of the outer annular surface of the head is disposed radially outward of the shank body.

5. The sacroiliac screw set forth in claim 4, wherein the entirety of the outer annular surface of the head is disposed radially outward of the at least one screw thread.

6. The sacroiliac screw set forth in claim 5, wherein the head has a radiused proximal edge between the proximal end and the outer annular surface.

7. The sacroiliac screw set forth in claim 6, wherein the head has a radiused distal edge between the distal end and the outer annular surface.

8. The sacroiliac screw set forth in claim 7, wherein the proximal end of the head defines an opening leading to a passage extending through the head.

9. The sacroiliac screw set forth in claim 1, wherein the head is configured to be received in a washer.

10. The sacroiliac screw set forth in claim 1, in combination with a washer configured to be received on the head.

11. The sacroiliac screw set forth in claim 10, wherein the washer is configured to snap onto the head.

12. The sacroiliac screw set forth in claim 10, wherein the washer has a proximal end margin defining a plurality of axially-extending slots spaced apart circumferentially, and a distal end margin defining a plurality of teeth spaced apart circumferentially.

13. The sacroiliac screw set forth in claim 10, wherein the washer has an interior with a concave cross section.

14. The sacroiliac screw set forth in claim 13, wherein the head of the screw is configured to engage the interior of the washer to enable pivoting of the washer on the head.

15. A sacroiliac screw assembly comprising:
a sacroiliac screw including
a tip,
a head,
a shank extending distally from the head to the tip, the shank including a shank body and open-cell metal foam at least partially covering the shank body, and
at least one screw thread circumscribing the shank,
wherein the tip, the head, the shank, and the at least one screw thread are integrally formed as a one-piece, monolithic component by additive manufacturing,
wherein the sacroiliac screw is configured to be implanted into the ilium bone and through the sacroiliac joint,
wherein the head has a frustoconical shape having an outer annular surface tapering from a proximal end to a distal end of the head; and
a washer received on the head.

16. The sacroiliac screw assembly set forth in claim 15, wherein an entirety of the head is received in the washer.

17. The sacroiliac screw assembly set forth in claim 16, wherein the washer is snap-fit on the head.

18. The sacroiliac screw assembly set forth in claim 17, wherein the washer has a proximal end margin defining a plurality of axially-extending slots spaced apart circumferentially, and a distal end margin defining a plurality of teeth spaced apart circumferentially.

19. The sacroiliac screw assembly set forth in claim 18, wherein the washer has an interior with a concave cross section.

20. The sacroiliac screw assembly set forth in claim 19, wherein the head of the screw is configured to engage the interior of the washer to enable pivoting of the washer on the head.

* * * * *